United States Patent
Ihde, II

(10) Patent No.: US 9,603,753 B2
(45) Date of Patent: Mar. 28, 2017

(54) FLUID ABSORBENT SURGICAL DEVICE FOR CANNULAS

(71) Applicant: Glenn M. Ihde, II, Red Oak, TX (US)

(72) Inventor: Glenn M. Ihde, II, Red Oak, TX (US)

(*) Notice: Subject to any disclaimer, the term of this patent is extended or adjusted under 35 U.S.C. 154(b) by 384 days.

(21) Appl. No.: 14/333,508

(22) Filed: Jul. 16, 2014

(65) Prior Publication Data

US 2016/0015573 A1     Jan. 21, 2016

(51) Int. Cl.
| | | |
|---|---|---|
| A61M 1/00 | (2006.01) | |
| A61B 17/34 | (2006.01) | |
| A61F 13/38 | (2006.01) | |
| A61B 1/00 | (2006.01) | |
| A61B 90/70 | (2016.01) | |

(52) U.S. Cl.
CPC .......... *A61F 13/38* (2013.01); *A61B 1/00131* (2013.01); *A61B 90/70* (2016.02); *A61B 2090/701* (2016.02)

(58) Field of Classification Search
CPC .......... A61B 1/00131; A61B 2090/701; A61B 90/70; A61F 13/38
See application file for complete search history.

(56) References Cited

U.S. PATENT DOCUMENTS

| | | | |
|---|---|---|---|
| 724,913 A * | 4/1903 | Montgomery | A61M 25/04 137/854 |
| 3,149,360 A | 9/1964 | Lend | |
| 3,818,911 A | 6/1974 | Fournier | |
| 3,850,754 A | 11/1974 | Wilkins et al. | |
| 5,084,005 A | 1/1992 | Kachigian | |
| 5,147,288 A | 9/1992 | Schiavo | |
| 5,188,630 A | 2/1993 | Christoudias | |
| 5,339,828 A * | 8/1994 | Keating | A61B 10/04 600/562 |
| 5,392,766 A | 2/1995 | Masterson et al. | |
| 5,407,423 A | 4/1995 | Yoon | |
| 5,518,502 A | 5/1996 | Kaplan et al. | |
| 5,599,292 A | 2/1997 | Yoon | |
| 5,700,239 A | 12/1997 | Yoon | |
| 5,715,559 A | 2/1998 | Mitri | |
| 6,277,090 B1 | 8/2001 | Crawford, Jr. | |
| 6,565,544 B1 * | 5/2003 | Rainin | A61M 1/008 604/289 |
| 6,923,760 B2 | 8/2005 | Koda et al. | |
| 7,112,184 B2 | 9/2006 | Bichsel et al. | |

(Continued)

FOREIGN PATENT DOCUMENTS

WO     2008028187 A2     3/2008

OTHER PUBLICATIONS

Foreign Communication from a Related Counterpart Application—International Search Report and Written Opinion, PCT/US22007/077532, Mar. 17, 2008, 10 pages.
Foreign Communication from a Related Counterpart Application—International Preliminary Report on Patentability, PCT/US22007/077532, Mar. 12, 2009, 8 pages.
Office Action dated Sep. 28, 2010, U.S. Appl. No. 11/848,896.
Final Office Action dated Mar. 16, 2011, U.S. Appl. No. 11/848,896.
Notice of Allowance dated Mar. 14, 2013, U.S. Appl. No. 11/848,896.

(Continued)

*Primary Examiner* — Michele M Kidwell

(57) ABSTRACT

A surgical device that absorbs fluid material on a surface of a cannula comprises a handle, and an absorbent portion coupled to a first end of the handle. The absorbent portion comprises a plurality of absorbent discs separated by at least one spacer. The plurality of absorbent discs and the at least one spacer are disposed about a post, and the at least one spacer is restrained from axial movement relative to the post.

19 Claims, 9 Drawing Sheets

(56) References Cited

U.S. PATENT DOCUMENTS

| | | |
|---|---|---|
| 7,211,061 B1 | 5/2007 | Maxwell |
| 8,480,699 B2 | 7/2013 | Ihde |
| 8,764,783 B2 | 7/2014 | Ihde, II |
| 9,205,469 B2 | 12/2015 | Ihde, II |
| 2003/0181840 A1 | 9/2003 | Tsaur |
| 2004/0204671 A1 | 10/2004 | Stubbs et al. |
| 2006/0003182 A1 | 1/2006 | Lane et al. |
| 2006/0084983 A1 | 4/2006 | Kim |
| 2008/0058852 A1* | 3/2008 | Ihde .................. A61B 90/70 606/185 |
| 2011/0230853 A1* | 9/2011 | Ihde, II ............. A61B 17/3421 604/385.01 |

OTHER PUBLICATIONS

FAIPP Pre-Interview Communication dated Jun. 20, 2013, U.S. Appl. No. 13/151,240, filed Jun. 1, 2011.

FAIPP Office Action dated Sep. 4, 2013, U.S. Appl. No. 13/151,240, filed Jun. 1, 2011.

Notice of Allowance dated Feb. 18, 2014, U.S. Appl. No. 13/151,240, filed Jun. 1, 2011.

Ihde II, M.D., Glenn M., Patent Application entitled "Fluid Absorbent Surgical Device for Cannulas", filed May 16, 2014, U.S. Appl. No. 14/279,739.

FAIPP Pre-Interview Communication dated Jul. 1, 2015, U.S. Appl. No. 14/279,739, filed May 16, 2014.

Notice of Allowance dated Oct. 16, 2015, U.S. Appl. No. 14/279,739, filed May 16, 2014.

* cited by examiner

FLUID ABSORBENT SURGICAL DEVICE FOR CANNULAS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Laparoscopic surgery is a form of minimally invasive, endoscopic surgery performed in the abdomen. With laparoscopic surgery, general anesthesia is given. A small incision is usually made below or inside the umbilicus. The abdomen is then insufflated with an inert gas, such as carbon dioxide, by inserting a special needle (e.g., a trocar) used to insert a cannula through the umbilicus. Insufflation induces a state of pneumoperitoneum, which enhances the surgeon's view and ability to make manipulations. If a special needle is used, the surgeon removes the needle after an adequate volume of gas is insufflated into the abdominal cavity and inserts a cannula. The valve in the cannula prevents the inert gas from escaping through the cannula. This helps to maintain the state of pneumoperitoneum. An endoscope, also called a laparoscope, is then placed through the cannula. The laparoscope allows the surgeon to visualize the pelvic and abdominal organs on a video monitor. Additional smaller incisions are made in the abdomen to allow placement of additional cannulas as needed. The additional cannulas are for the surgeon to place specially designed surgical instruments into the abdominal cavity, allowing the surgeon to carry out the same procedure as in open surgery.

For patients, the advantages of laparoscopic surgery over open surgery include reduced trauma to the body, reduced blood loss, and smaller surgical scars. Patients also leave the hospital sooner after a laparoscopic procedure and return to normal activities sooner than with conventional open surgery. Similar minimally invasive approaches, such as thoracoscopic surgery, may be performed on other areas of the body. These approaches share some of the same advantages and challenges as laparoscopic surgery.

SUMMARY

In an embodiment, a surgical device that absorbs fluid material on a surface of a cannula comprises a handle, and an absorbent portion coupled to a first end of the handle. The absorbent portion comprises a plurality of absorbent discs separated by at least one spacer. The plurality of absorbent discs and the at least one spacer are disposed about a post, and the at least one spacer is restrained from axial movement relative to the post.

In an embodiment, a surgical device that absorbs fluid material on a surface of a cannula comprises a handle, and an absorbent portion coupled to a first end of the handle. The absorbent portion comprises a plurality of absorbent discs separated by at least one spacer, and a ratio of a length of a first absorbent disc of the plurality of absorbent disc to an outer diameter of the first absorbent disc is in a ratio of between about 1:2 and about 3:1.

In an embodiment, a surgical device that absorbs fluid material on a surface of a cannula comprises a handle, and an absorbent portion coupled to a first end of the handle. The absorbent portion comprises a plurality of absorbent discs separated by at least one spacer. The at least one spacer has a first edge, and the first edge has an outer diameter that is reduced relative to a maximum outer diameter of the at least one spacer.

In an embodiment, a method of absorbing fluid in a cannula comprises disposing a surgical instrument into a cannula, contacting an absorbent portion with a fluid disposed on a surface of the cannula, and absorbing at least a portion of the fluid with the absorbent portion. The surgical device comprises an absorbent portion comprising a plurality of absorbent discs separated by at least one spacer, and the at least one spacer is restrained from axial movement relative to the plurality of absorbent discs.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
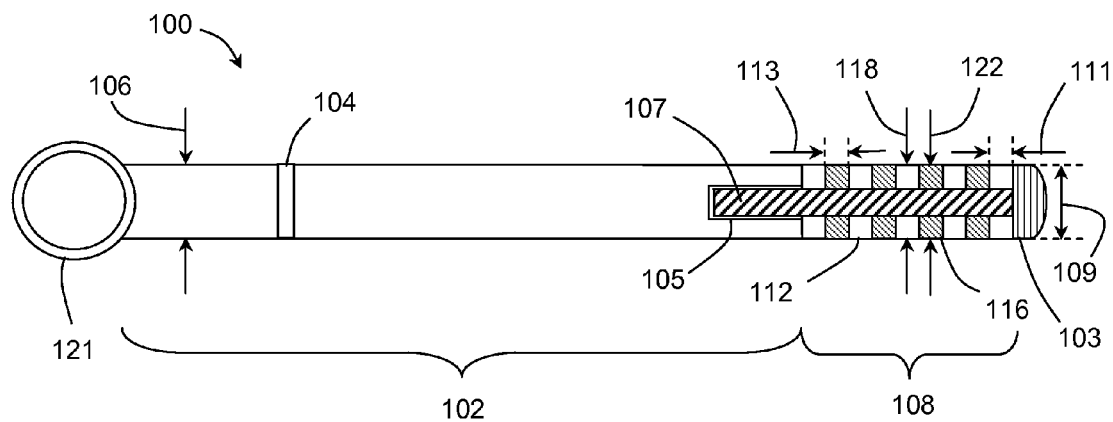
FIG. 1 illustrates a cross-sectional view of an embodiment of a surgical device.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The key element in laparoscopic surgery is the use of a laparoscope to view and illuminate the operative field. The laparoscope comprises a telescopic rod lens system that is connected to a video camera (single chip or three chip). The rod is made of a light conducting material that is used to pass the image from the tip of the rod to the camera head. The rod is passed through the cannula and into the abdominal cavity where it transmits the light and images from inside the abdomen to the camera. The camera then transmits the light and images to a video monitor for viewing.

A trocar, also called a trocar sleeve or cannula, is a specially designed tube, usually 3 mm, 5 mm, 10/11 mm, 12 mm, or 15 mm in diameter, with a valve through which a surgeon can insert special instruments. While described as having certain sizes, various other diameters are also possible and generally range between about 2 mm and about 20 mm. In general, a trocar can refer to the device used to insert the cannula into the body of a patient. While the trocar sleeve may be made from several components, reference will be made to a cannula herein, which may refer to both the trocar and/or the cannula. At the outer end (e.g., the end outside the body of the patient) of the cannula, the valve may maintain the inert gas from escaping. In some embodiments, the valve comprises a two stage valve system including an inner valve and an outer valve where the inner valve is closer to the body of the patient. The purpose of the two stage system is to create two sealing points to allow for insertion and/or removal of an instrument without allowing significant fluid leakage through the valve system. The inner valve can comprise a leaflet design bi-valve, and the outer valve can comprise a circular seal the size of the intended instrument. In some embodiments, the outer valve can be made from multiple wedge shaped leaflets to allow more than one size of instrument to be used while still maintaining a seal with the instrument.

When the laparoscope passes through the valve and the cannula, fluid materials deposited on the cannula during the course of an operation have a tendency to contact the lens of the laparoscope and obscure the view of the camera. Fluid materials can pass onto the lens as it passes through the valve and/or as it passes through the inner walls of the cannula. Fluid materials along the inner walls and the tip of the cannula can transfer to the lens by way of capillary action due to the fluid material's surface tension.

When fluid materials obscure the lens, the laparoscope can be removed from inside the cannula, and the lens is cleaned outside of the abdominal cavity. However, as long as fluid materials remain inside the cannula, the lens will become obscured immediately upon re-insertion into the cannula. Again, the laparoscope will then be removed from inside the cannula, and the lens cleaned outside of the abdominal cavity. This process is repeated several times until the lens no longer becomes obscured with fluid materials. Cleaning the lens repeatedly until it no longer becomes obscured with fluid materials increases the total time that it takes to perform the laparoscopy. This increases the amount of time that the patient is under anesthesia as well as the amount of time the instruments are inside the abdominal cavity without being directly visualized.

Accordingly, the disclosure teaches a surgical device for keeping a laparoscopic lens free of obstructing fluid materials by absorbing fluid material from the surfaces of the cannula. The surgical device includes an absorbent portion that absorbs fluid material from the surfaces of the cannula, including the valves, the inner wall, a distal tip of the cannula, and an outer wall of the cannula. In one embodiment, the absorbent portion comprises a plurality of absorbent discs. The plurality of absorbent discs may be separated by one or more spacers. When the absorbent portion of the surgical device is inserted inside the cannula, the absorbent portion absorbs fluid material along any valve that it passes through and along the inner wall of the cannula. The absorbent portion may also absorb fluid material along the outer wall of the cannula as it passes through the tip of the cannula.

As the absorbent discs pass through the cannula, they may absorb the fluid. Any subsequent compression of the absorbent discs may result in the fluid being emitted from the absorbent discs as the compression squeezes the fluid out of the absorbent material. In order to avoid the compression of the absorbent discs, the spacers may be fixed in position. For example, the spacers may be adhered to a central post, which may limit or prevent any axial movement of the spacers relative to the absorbent discs. This may limit or prevent any compression on the absorbent discs resulting from movement of the spacers. Further, one or more edges of the spacers may be tapered, chamfered, or the like to reduce the chances that an edge of the spacer catches on an opening or restriction in the cannula. This may also reduce the likelihood that the absorbent discs are compressed by the spacers.

The absorbent discs may also be designed to reduce the compression of the absorbent disc caused by the interaction of the absorbent discs with the inner walls of the cannula. As the absorbent discs move along the wall of the cannula, the outer surface may contact the inner surface of the cannula and create a tangential force on the absorbent discs. This may cause the absorbent discs to bunch up or otherwise axially compress. In order to limit this type of compression, the discs may be designed such that their thickness is limited to avoid excessive compression caused by tangential or drag forces. For example, a ratio of a length of the absorbent disc to an outer diameter of the absorbent disc may be in a ratio of between about 1:2 and about 3:1. This may avoid excessive compression caused by the tangential forces that can be associated with an absorbent disc having an excessive length relative to its outer diameter.

Because the surgical device of the disclosure absorbs fluid material from inside the cannula, it may be used to reduce the number of passes needed to remove fluid materials from the laparoscopic lens. Reducing the number of passes reduces the total time that it takes to perform the laparoscopy, which reduces the amount of time that the patient is under anesthesia as well as the amount of time the instruments are inside the abdominal cavity without being directly visualized.

FIG. 1 illustrates a cross-sectional view of an embodiment of a fluid absorbent surgical device 100. The fluid absorbent surgical device 100 illustrated in FIG. 1 may comprise a handle 102 and an absorbent portion 108. The absorbent portion 108 may comprise a plurality of absorbent discs 112, a plurality of spacers 116, and an end cap 103. The absorbent portion 108 may comprise a central post 107 coupled to the end cap 103. The plurality of absorbent discs 112 and the plurality of spacers 116 may be disposed about the post 107, and the handle 102 may comprise a generally elongated member having an opening or hole 105 configured to receive the post 107. When the plurality of plurality of absorbent discs 112 and the plurality of spacers 116 are disposed about the post 107 and the post 107 is received within the opening 105, the plurality of absorbent discs 112 and the plurality of spacers 116 can be retained about the post 107 between the end cap 103 and the handle 102.

In an embodiment, the handle 102 may have a generally cylindrical cross section with a central axis. In some embodiments, the handle 102 may also be formed with other cross section shapes include square, rectangular, oval, polygonal, or the like. The opening in the handle 102 may be configured to receive the post 107, and the post 107 and the opening 105 may have corresponding shapes. As described in more detail here, the post 107 may be retained in the opening 105 by a compression fit, an adhesive, a mechanical engagement (e.g., threaded engagement, splined engagement, etc.), or the like.

The handle 102 may have a length sufficient to allow the surgical device 100 to be introduced into a cannula while being held so that the absorbent portion 108 extends at least to the end of the cannula, and in some embodiments, slightly past the end of the cannula within the body. In an embodiment, the handle 102 may be between about 10 cm and about 40 cm, or between about 15 cm and about 30 cm in length. In an embodiment, the handle 102 is about 18 cm to about 21 cm in length. The diameter 106 of the handle 102 may be sized to allow the handle to be inserted within the cannula, and as a result, the outer diameter of the handle 102 may be less than the inner diameter of the cannula in which the surgical device 100 is to be used. The diameter 106 of the handle 102 may be less than the inner diameter of the cannula by an amount sufficient to allow the free movement of the surgical device 100 within the cannula. In an embodiment, the diameter 106 of the handle 102 may be between about 3 mm and about 15 mm, or between about 5 mm and about 10 mm. In an embodiment, the diameter 106 of the handle 102 may be about 3 mm, about 5 mm, about 10 mm, about 11 mm, about 12 mm, or about 15 mm, and the diameter may correspond to the diameter 106 of the cannula in which the surgical device 100 is to be used.

The handle 102 can be formed of various types of materials. As a surgical device, the handle 102 may be sterilized using a variety of techniques, and the materials used to form the handle 102 can be selected to allow the handle to be sterilized prior to use. In an embodiment, the handle 102 can be made, for example, from a type of plastic that is commonly used in many surgical devices. Various plastics may be suitable including, but not limited to, acetal polymers, polyethylene (e.g., high-density polyethylene), a polyamide, a polycarbonate, a polyethermide, a polyphenylsulfone, a polypropylene, nitrile polymers, or any combination thereof. In some embodiments, the handle may be formed from a metal, ceramic (e.g., glass, etc.), a composite material (e.g., fiberglass), or any combination thereof.

In an embodiment, an optional marker 104 can be used with any embodiment disclosed herein. The marker 104 can be used to indicate an insertion distance for inserting the surgical device 100 inside a cannula. The insertion distance may be selected to allow at least a portion of any fluid along the outer wall of the distal tip of a cannula to be absorbed without allowing the absorbent portion to be inserted far enough to become saturated by coming into significant contact with fluid material that is not gathered on the cannula surfaces. Significant contact may be taken as having more than fifty percent of the absorbed fluid materials come from contact with bodily fluids that are not gathered on the surfaces of the cannula. For example, the optimal distance may be from about 28 cm to about 30 cm between the marker and the end of the end cap 103 for a cannula with a length of about 29 cm. The marker 104 may comprise any type of structure or indication suitable to illustrate the insertion distance. As shown in FIG. 1, the marker 104 may comprise a stripe, an indention, a protrusion, or other indicator (e.g., a dot, spaced pattern, or the like). In some embodiments, the marker 104 may extend at least partially about the handle 102. In an embodiment, the marker 104 may comprise a portion of material having a different color than the remainder of the handle 102 and/or a separate material may be disposed on the handle 102 to form the marker 104. In some embodiments, a protrusion (e.g., wedge 202 of FIG. 2) may be formed on the handle 102 to form the marker.

In some embodiments, the surgical device 100 may comprise a grip 121. The grip 121 may serve as a grasping point or feature to allow the surgical device to be held during use. The grip 121 may be provided at an end of the handle 102, though the grip 121 may also be disposed along the length of the handle 102. The grip 121 may be formed as an integral part of the handle 102 or may be formed separately from the handle 102. The grip 121 may be formed from any of the materials used to form the handle 102, and the grip 121 may comprise the same material as the handle 102 or a different material. In some embodiments, a non-slip material or coating may be used to form the grip 121.

In an embodiment, the absorbent portion 108 of the surgical device 100 comprises a plurality of absorbent discs 112, a plurality of spacers 116, and an end cap 103. As noted above, the plurality of absorbent discs 112 and the plurality of spacers 116 may be disposed about the post 107. In an embodiment, the post 107 may comprise a generally circular cross section and be received within the opening having a corresponding cross sectional shape. The post 107 may be formed from the same material as the handle 102 or a different material than the handle 102. When an adhesive is used to attach the post 107 to the handle 102, the adhesive and the materials of construction for the handle 102 and the post 107 may be compatible so that the adhesive can bond the post 107 to the interior surface of the opening 105. The post 107 may be inserted into the opening 105 within the handle 102 a distance sufficient to provide a structural support of the post 107 and the absorbent portion 108. As a result, the distance to which the post 107 is inserted into the opening 105 may vary based on the type of adhesive, the type of engagement (e.g., bonded, interference fit, etc.), and the like. In an embodiment, the post 107 may be inserted into the opening 105 between about 0.5 cm and about 5 cm, or between about 1 cm and about 4 cm.

While illustrated as having a smooth outer surface, other structures may be used to allow the post 107 to engage and be retained within the opening 105. For example, the post 107 and the opening 105 may comprise complimentary threads to allow the post 107 to be screwed into the opening 105. In some embodiments, the post 107 may comprise splines, fluting or the like to allow the post to be inserted and retained within the opening by an interference fit, though an adhesive may also be used. In some embodiments, the post 107 and/or the opening 105 may have teeth (e.g., one-direction ratchet teeth) to allow the post 107 to be inserted into the opening 105 using an insertion force and retained in engagement within the opening 105 by a larger retraction force based on the interaction of the teeth. Further, it should be understood that the structures can be reversed with the same effect. For example, the handle 102 may comprise a reduced diameter extension acting as the post that engages an opening on the end cap 103.

The post 107 may have a diameter that is less than the diameter of the handle 102 to allow the plurality of absorbent discs 112 and the plurality of spacers 116 to be disposed about the post 107. In an embodiment, the post 107 may have a diameter of at least about 1 mm, at least about 2 mm, at least about 3 mm, or at least about 4 mm. In an embodiment, the post 107 may have a diameter of less than about 13 mm, less than about 10 mm, less than about 7 mm, or less than about 5 mm. The diameter of the post 107 may be sized to take into account the forces on the post created by movement of the surgical device 100 within the cannula. For example, the forces on the post may increase as the diameter of the cannula increases. In order to reduce the likelihood that the post may break in response to the forces, a ratio of the diameter of the post to the diameter of the handle may be at least about 0.1, at least about 0.2, or at least about 0.3. However, as the ratio of the diameter of the post to the diameter of the handle increases, the absorbent capacity of the absorbent discs may be reduced. In some embodiments, the ratio of the diameter of the post to the diameter of the handle may be less than about 0.9, less than about 0.8, less than about 0.7, less than about 0.6, or less than about 0.5. The length of the absorbent portion 108 may be sufficient to allow a desired number of absorbent discs 112 and/or a total absorbent capacity to be placed on the end of the surgical device 100. In some embodiments, the absorbent portion 108 may have a length between about 1 cm and about 5 cm, or between about 2 cm and about 4 cm.

The plurality of absorbent discs 112 and the plurality of spacers 116 may be inserted onto the post 107. The end cap 103 may secure the plurality of absorbent discs 112 and the plurality of spacers 116 about the post 107 between the end cap 103 and the handle 102. In an embodiment, the end cap 103 can be formed from any of the materials used to form the handle, and the end cap 103 can comprise the same material or a different material than the handle 102 and/or the post 107. In some embodiments, the end cap 103 may be made from a non-absorbent material. In some embodiments, the end cap 103 may be made of an absorbent material such as sterile cotton, foam, or the like. The end cap 103 may be rounded to enable easier and smoother transition of the fluid absorbent surgical device 100 into and out of the cannula.

In an embodiment, as is illustrated in FIG. 1, the plurality of absorbent discs 112 and the plurality of spacers 116 are alternated along the length of the post 107 so that each absorbent disc 112 may be separated by a spacer 116. Separating each of the plurality of absorbent discs 112 with at least one of the plurality of spacers 116 may help to limit expansion of the plurality of absorbent discs 112 in response to absorbing fluid as well as reduce leakage of the collected fluid material from the plurality of absorbent discs 112. While five absorbent discs 112 and four spacers 116 are shown in FIG. 1 alternated with each other, one of ordinary skill will appreciate that any number of absorbent discs 112 and spacers 116 may be inserted onto the second part 108 of the handle 102 in a number of different orientations without departing from the scope of the disclosure.

The outer diameter 118 of the plurality of absorbent discs 112 may approximate the inner diameter of the cannula through which the fluid surgical device 100 is going to be inserted such that the outer diameter 118 of the plurality of absorbent discs 112 can come into contact with a meniscus of a drop of fluid residing on the inner surface of the cannula thereby allowing absorbance of the drop of fluid. Similarly, the outer diameter 122 of the plurality of spacers 116 may also approximate the inner diameter of the cannula through which the fluid surgical device 100 is going to be inserted. In an embodiment, the outer diameter 118 of the plurality of absorbent discs 112 and/or the outer diameter 122 of the plurality of spacers 116 approximating the inner diameter of the cannula means that the absorbent discs 112 and/or the plurality of spacers 116 are of a size such that they may come into contact with the inside of the cannula when inserted therein. In another embodiment, the outer diameter 118 of the plurality of absorbent discs 112 and/or the outer diameter 122 of the plurality of spacers 116 approximating the inner diameter of the cannula means that the plurality of absorbent discs 112 and/or the plurality of spacers 116 may be of a size such that they do not have to come into full contact with the cannula when inserted therein. For example, the outer diameter 118 of the plurality of absorbent discs 112 and/or the outer diameter 122 of the plurality of spacers 116 may be slightly less than the inside of the diameter of the cannula. In this embodiment, absorption of a fluid by an absorbent disc 112 may be enabled by capillary action. Stated differently, capillary action may enable one or more of the plurality of absorbent discs 112 to substantially absorb the fluid materials inside the cannula without contacting the inside of the cannula.

As illustrated in FIG. 1, the outer diameter 118 of one or more of the plurality of absorbent discs 112 and the outer diameter 122 of one or more of the plurality of spacers 116 may be approximately equivalent to the diameter 106 of the handle 102. Additionally, the end cap 103 may comprise an outer diameter 109 that is approximately equivalent to the diameter 106 of the handle 102. For example, the outer diameters of the absorbent discs 112, the plurality of spacers 116, and/or the end cap 103 may be between about 3 mm and about 15 mm, or between about 5 mm and about 10 mm. In an embodiment, the outer diameters of the absorbent discs 112, the plurality of spacers 116, and/or the end cap 103 may be about 5 mm or about 10 mm. Having the outer diameters of the absorbent discs 112, the plurality of spacers 116, the handle 102, and/or the end cap 103 be approximately equivalent creates a fluid absorbent surgical device 100 with a smooth surface, which helps to reduce the likelihood of the fluid absorbent surgical device 100 catching an edge of the cannula and pulling the cannula out of the body.

In some embodiments, the outer diameter 118 of the plurality of absorbent discs 112 may be slightly smaller than the outer diameter 122 of the plurality of spacers 116. In such embodiments, capillary action may enable the plurality of absorbent discs 112 to absorb the fluid from the inside surface of the cannula. Also, such embodiments may enable the plurality of absorbent discs 112 to expand if necessary after absorbing the fluid without allowing the plurality of absorbent discs 112 to expand beyond the outer diameter 122 of the plurality of spacers 116 thereby reducing the likelihood that the plurality of absorbent discs 112 will leak absorbed fluids as the fluid absorbent surgical device 100 is pulled out of the cannula.

The plurality of absorbent discs 112 may be made of an absorbent material. In a preferred embodiment, the plurality of absorbent discs 112 are made of an absorbent material having a limited or substantially non-existent expansion upon absorbing a fluid. Such an embodiment avoids redistribution or leakage of the collected fluid materials from one or more of the plurality of absorbent discs 112 as the fluid absorbent surgical device 100 is being moved through the cannula. Additionally, such an embodiment helps to reduce the chances that one of the plurality of absorbent discs 112 will expand to such degree that it catches an edge of the cannula and causes the cannula to move or be pulled from the body. In an embodiment, the plurality of absorbent discs 112 are made of foam. Any suitable foam may be used such as a polymeric foam. The foam may generally comprise an open cell foam to allow the fluid to be absorbed into the absorbent disc 112. The foam may also be hydrophilic to allow aqueous fluids to wick into the foam. In an embodiment, one or more of the plurality of absorbent discs 112 may be made of polyvinyl acetate (PVA) foam. In some embodiments, one or more of the plurality of absorbent discs 112 may be made of sterile cotton, cellulosic material, or any other absorbent material. Each of the plurality of absorbent discs 112 may comprise the same materials or different materials.

In some embodiments, an optional additive may be disposed on one or more of the plurality of absorbent discs 112. Various chemicals may be used to clean the cannula, remove a fluid component, aid in the prevention of fluid accumulation, or the like. For example, a saline solution may be disposed on one or more of the plurality of absorbent discs 112, for example, the absorbent disc closest to the end cap 103. The saline solution may be used to wash the inside of cannula to help remove any fluid. The remaining absorbent discs 112 may then absorb any saline solution and/or any other fluids. Other solutions such as surfactants, cleaning solutions, and/or defogging solutions for the lens may also be disposed on one or more of the absorbent discs 112 prior to disposing the surgical device 100 into the cannula during use.

In general, the absorbent discs 112 may be compressible to allow for fluid absorption. Any axial compression of the absorbent discs 112 may decrease the absorbent capacity of the absorbent disc 112 and cause a portion of the fluid absorbed by the absorbent disc 112 to be emitted or expelled from the absorbent disc 112. The axial compression can occur as a result of an axial or tangential drag force on the outer surface of the absorbent disc 112 as it contacts the inner surface of the cannula and/or one or more of the valves as the surgical device 100 is translated within the cannula. For example, the absorbent material may drag on the interior surface of the cannula and tend to "bunch up" as it moves along. As the length of the absorbent disc 112 increases, so does the potential for the compression of the absorbent disc 112. Several factors may limit the likelihood and amount of compression of one or more of the absorbent discs 112 including, but not limited to, the length of the absorbent disc, the diameter of the absorbent disc, the type of material used to form the absorbent disc, the ability of the absorbent disc to move relative to the post 107, and/or the ability of one or more of the spacers 116 to move relative to the post 107.

The plurality of absorbent discs 112 may be disposed above the post 107 and retained in position by the spacers 116, the end of the handle 102, and/or the end cap 103. In some embodiments, one or more of the absorbent discs 112 may be coupled to the post 107 to prevent or limit any axial movement during movement within the cannula. For example, an absorbent disc 112 may be adhered to the post 107 using an adhesive such as a glue (e.g., epoxy), a double sided adhesive film, a thermoset adhesive, a thermoplastic, or the like to bond at least a portion of the interior surface of the absorbent disc 112 to the exterior surface of the post 107. In some embodiments, the absorbent discs 112 may be formed directly on the post 107, for example, using injection molding of the absorbent material between the spacers 116, or the like. Adhering the absorbent disc 112 to the post 107 may be useful when a longer absorbent disc 112 is used. In some embodiments, the absorbent discs 112 may not be adhered to the post 107. This may avoid any potential loss of absorbent capacity due to a chemical adherent being absorbed by the absorbent disc 112.

The spacers 116 may be disposed on the post and serve to separate the plurality of absorbent discs 112. The plurality of spacers 116 may comprise any shape suitable for separating the absorbent discs 112. In an embodiment, the spacers 116 may comprise beads, discs, cylinders, and the like. As used herein, the term "disc" refers to a generally circular object with a height or a thickness that is less than its total diameter (e.g., any generally circular object with some amount of dimensional flattening to make it less than a perfect sphere) and/or a generally cylindrical object. In an embodiment, one or more of the spacers 116 may be made of a non-absorbent material. For example, in an embodiment, the plurality of spacers 116 can be formed from any of the type of material used to form the handle 102. Each of the plurality of spacers 116 can comprise the same material or different materials. In an embodiment, one or more of the plurality of spacers 116 may comprise a non-absorbent polymer. Thus, in some embodiments, the plurality of spacers 116 may be considered a plurality of non-absorbent discs.

One or more of the plurality of spacers 116 can be adhered to the post 107 to prevent axial movement of the spacers 116 during use. When the absorbent discs 112 have absorbed fluid, any compression of the absorbent discs 112 may cause the fluid to be emitted from the absorbent disc 112. In order to avoid compression of the absorbent discs 112 during movement of the surgical device 100 within the cannula, the spacers 116 may be restrained from axial movement relative to the post 107. This may create a fixed space for the absorbent disc between adjacent spacers, between a spacer and the end cap 103, and/or between a spacer and the end of the handle 102. In some embodiments, all of the plurality of spacers 116 can be restrained from axial movement relative to the post 107. In some embodiments, one or more of the spacers 116 may not be coupled to the post 107.

One or more of the plurality of spacers 116 can be adhered to the post 107 to create a fixed engagement between the spacer(s) 116 and the post 107. In an embodiment, a spacer 116 may be adhered to the post 107 using an adhesive such as a glue (e.g., epoxy), a double sided adhesive film, a thermoset adhesive, a thermoplastic, or the like to bond the interior surface of the spacer 116 to the exterior surface of the post 107. In some embodiments, the spacer may be configured to engage an indicator, an indentation, and/or a protrusion on the exterior surface of the post 107 to prevent axial movement of the spacer 116 during use. In this embodiment, the spacer may be free to rotate about the post 107 while be constrained from axial movement unless an axial force above a threshold is applied to the spacer 116. The engagement structure can be configured to only release the spacer 116 at a force threshold substantially above that expected to be encountered during normal use. In some embodiments, the spacer 116 may be formed as part of the post 107. For example, the spacer 116 and the post 107 can be formed in a single injection process and/or may be integrally formed so as to be a single, unitary component. Any other structure suitable for restraining the spacer or spacers 116 from axial movement during movement of the surgical instrument within and/or into the cannula may also be used.

In an embodiment, the thickness 111 of the plurality of absorbent discs 112 and the thickness 113 of plurality of spacers 116 may be approximately the same. As used herein, the term "thickness" refers to a longitudinal length along the main axis of the surgical device 100. In an embodiment, the thickness 111 of the plurality of absorbent discs 112 and the thickness 113 of the plurality of spacers 116 may be between about 1 mm and about 20 mm, or between about 2 mm and about 15 mm. In some embodiments, the thickness 111 of the plurality of absorbent discs 112 and the thickness 113 of the plurality of spacers 116 may be about 3 mm. Alternately, the thickness 113 of plurality of spacers 116 may be greater than or less than the thickness 111 of the plurality of absorbent discs 112. Each absorbent disc 112 and/or spacer 116 can have the same thickness or a different thickness.

In an embodiment, a ratio of the thickness of the absorbent discs 112 to the outer diameter 118 of the absorbent discs 112 may affect the likelihood and amount of axial compression of the absorbent disc as it is translated through the cannula during use. In general, a relatively low ratio of the thickness of the absorbent discs 112 to the outer diameter 118 of the absorbent discs 112 may reduce the amount of any tangential force applied to the absorbent discs 112 but may also limit the absorbent capacity of the absorbent discs 112. A relatively high ratio of the thickness of the absorbent discs 112 to the outer diameter 118 of the absorbent discs 112 may result in axial compression due to a tangential/drag force during use. A balance may be achieved by considering the ratio of the thickness of the absorbent discs 112 to the outer diameter 118 of the absorbent discs 112. In an embodiment, the ratio of the thickness of the absorbent discs 112 to the outer diameter 118 of the absorbent discs 112 may be between about 1:3 and about 4:1, or between about 1:2 and about 3:1. In some embodiments, the ratio of the thickness of the absorbent discs 112 to the outer diameter 118 of the absorbent discs 112 may be between about 3:5 and about 3:1.

Figure 2:
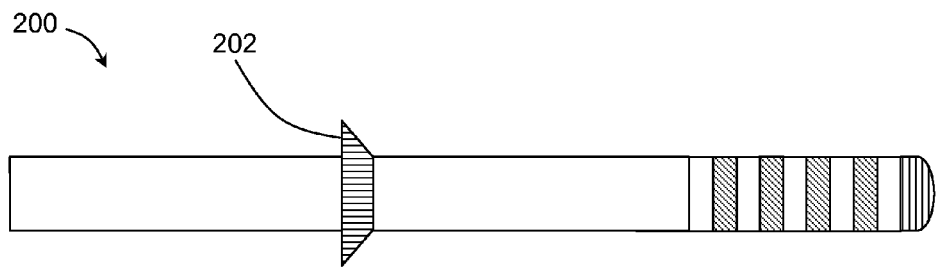
FIG. 2 illustrates a surgical device according to an embodiment of the disclosure.
Figure 3:
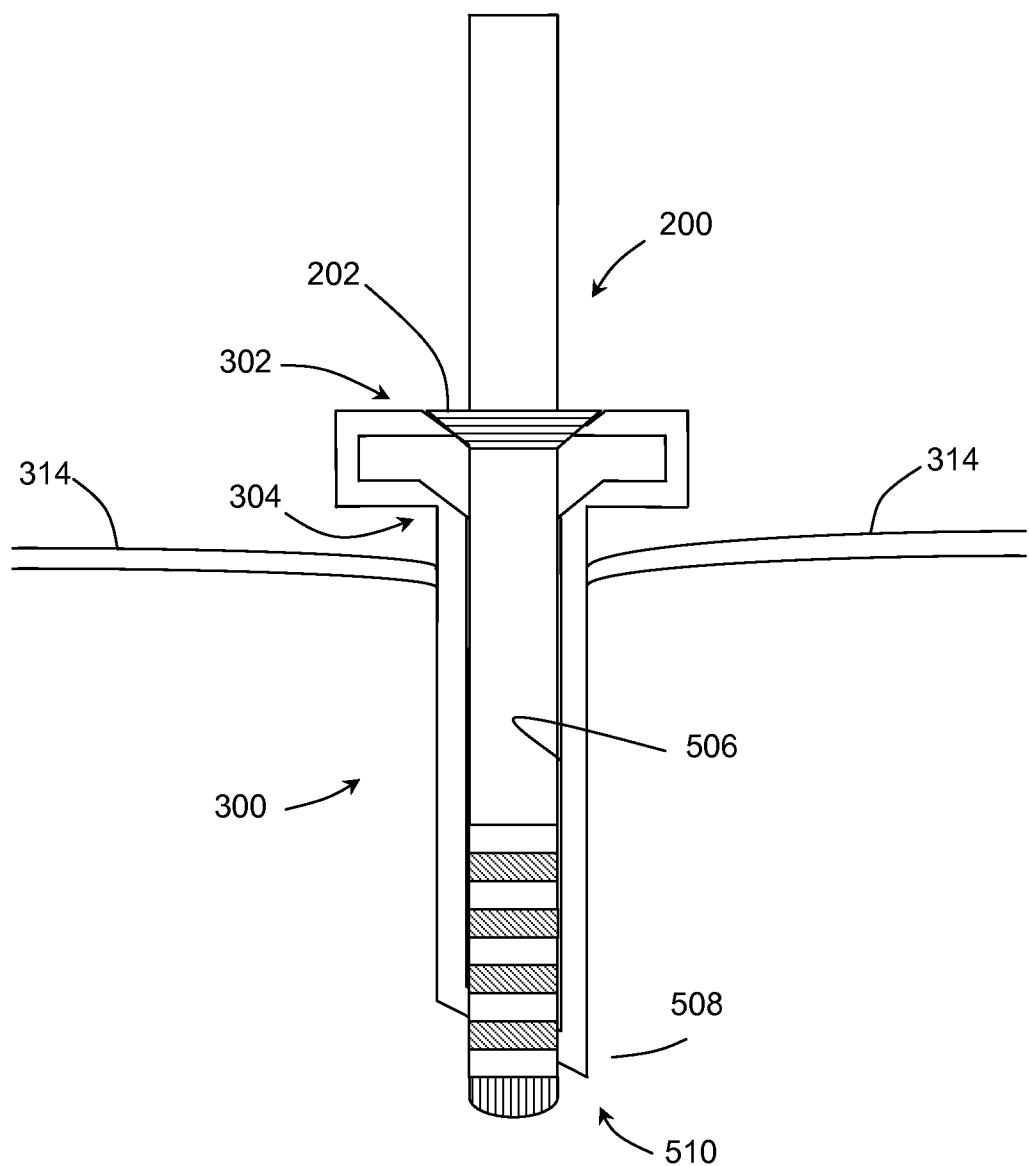
FIG. 3 illustrates a schematic view of a surgical device disposed within a trocar/cannula according to an embodiment of the disclosure.

FIGS. 2 and 3 illustrate another embodiment of a fluid absorbent surgical device 200. In an embodiment, the fluid absorbent surgical device 200 is similar to the fluid absorbent surgical device 100 illustrated in FIG. 1, and similar components will not be described with respect to FIGS. 2 and 3 in the interest of clarity. It should be understood that any of the embodiments and/or options described with respect to FIG. 1 can also be used with the surgical device 200. The surgical device 200 of FIGS. 2 and 3 is similar to the surgical device 100 of FIG. 1 except that the fluid absorbent surgical device 200 also comprises a wedge 202.

In an embodiment, the wedge 202 is positioned on the handle 102 to indicate an insertion distance for inserting the fluid absorbent surgical device 200 inside the cannula 300. The wedge 202 may be a part of the handle 102 or may be an addition to the handle 102. The trocar or cannula 300 comprises an outer valve 302, an inner valve 304, an inner wall 506, and an outer wall 508 of the distal tip 510 of a cannula 300 after it has been inserted across an abdominal wall 314. The distal end or tip 510 for the purposes of this disclosure refers to the end of the cannula that is inserted into the body cavity.

Referring to FIG. 3, the wedge 202 may be shaped such that it is not capable or not easily capable of being pushed through the outer valve 302. For example, the wedge 202 may act as a stopper hindering and/or preventing the fluid absorbent surgical device 200 from moving any further through the cannula 300 once the wedge 202 contacts the outer valve 302. In an embodiment, the wedge 202 may be positioned on the handle 102 such that one or more of the plurality of absorbent discs 112 and/or one or more of the plurality of spacers 116 are capable of protruding beyond the tip of the cannula 300. Such an embodiment may enable the fluid absorbent surgical device 200 to absorb fluid from the outer wall along a distal tip of the cannula 300. In some embodiments, the wedge 202 may be positioned on the handle 102 such that none of the plurality of absorbent discs 112 or the plurality of spacers 116 are capable of protruding beyond the tip of the cannula 300.

The wedge 202 may be made out of an absorbent material such as foam or cotton thereby enabling the wedge 202 to absorb fluids that have become deposited along the outer valve 302. Alternatively, the wedge 202 may be made of a non-absorbent material such as a type of plastic that is commonly used in many surgical devices. In some embodiments, other markers may be used in place of the wedge 202. Other forms of the markers (e.g., marker 104 of FIG. 1) may be used to indicate the insertion distance so that the marker 104 can be aligned with the outer valve 302 to indicate the maximum insertion distance.

Figure 4:
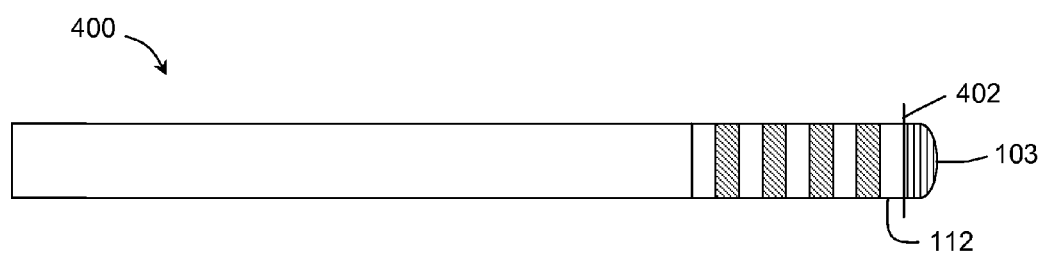
FIG. 4 illustrates another surgical device according to an embodiment of the disclosure.
Figure 5A:
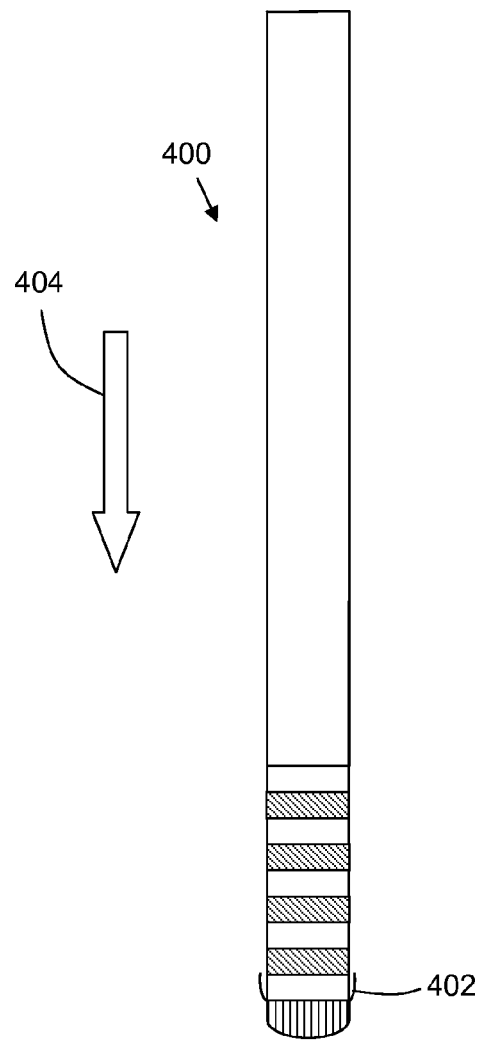
FIGS. 5A and 5B illustrate another view of a surgical device according to an embodiment of the disclosure.
Figure 5B:
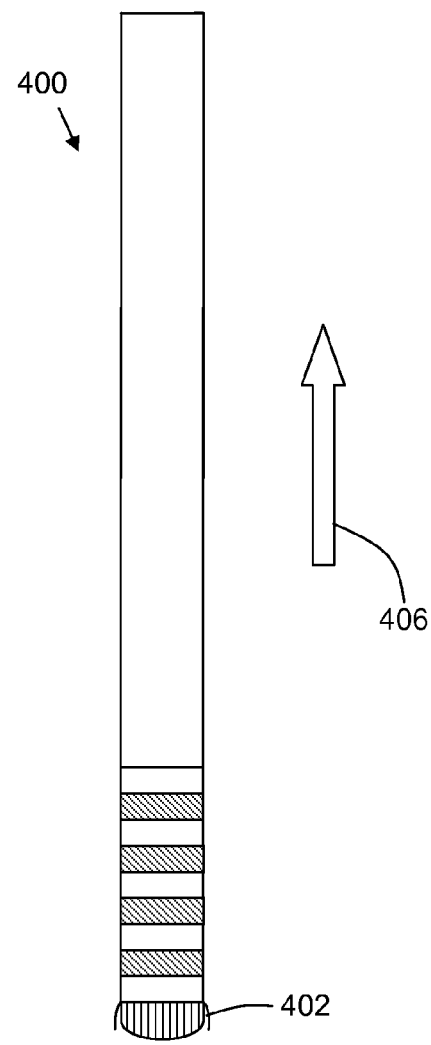

FIGS. 4, 5A, and 5B illustrate another embodiment of a fluid absorbent surgical device 400. In an embodiment, the fluid absorbent surgical device 400 may be similar to the fluid absorbent surgical device 100 illustrated in FIG. 1 and/or the surgical device 200 illustrated in FIGS. 2 and 3, and similar components will not be described with respect to FIGS. 4, 5A, and 5B in the interest of clarity. It should be understood that any of the embodiments and/or options described with respect to FIGS. 1-3 can also be used with the surgical device 400. In an embodiment, the fluid absorbent surgical device 400 is similar to the fluid absorbent surgical device 100 illustrated in FIG. 1 and/or the fluid absorbent surgical device 200 illustrated in FIGS. 2 and 3 except that the fluid absorbent surgical device 400 also comprises a flexible disc 402.

The flexible disc 402 may be positioned about the post 107 in the absorbent portion 108. For example, the flexible disc 402 may be positioned between an absorbent disc 112 and the end cap 103. In an embodiment, the flexible disc 402 can be formed from a flexible material that enables the flexible disc 402 to dome, fold, or otherwise deform in response to an applied force. For example, the flexible disc 402 may be made of a flexible, non-absorbent material such as plastic.

In an embodiment, the flexible disc 402 comprises a diameter that is larger than the inside diameter of the cannula. For example, the flexible disc 402 may comprise an outer diameter that is greater than or equal to the outside diameter of the cannula. Additionally, the flexible disc 402 may comprise a thickness that enables the flexible disc to flex around at least part of an absorbent disc 112 as the fluid absorbent surgical device 400 is inserted into the cannula (e.g., traveling in the direction indicated by arrow 404 illustrated in FIG. 5A) and at least part of the end cap 103 as the fluid absorbent surgical device 400 is removed from the cannula (e.g., traveling in the direction indicated by arrow 406 illustrated in FIG. 5B). For instance, the flexible disc 402 may be thinner than the plurality of absorbent discs 112 and the plurality of spacers 116. In some embodiments, the diameter of the absorbent disc 112 and the end cap 103 may be reduced in order to allow the flexible disc 402 to fold around the absorbent disc 112 and the end cap 103 as the fluid absorbent surgical device 400 is inserted into and pulled out of the cannula. Also, in some embodiments, the thickness of the absorbent disc 112 may be reduced to enable the flexible disc 402 to cover most or the entire absorbent disc 112 adjacent the flexible disc 402.

Referring to FIG. 5A, as the fluid absorbent device 400 is inserted into the cannula, the flexible disc 402 may shield or cover some or substantially all of the absorbent disc 112 adjacent the flexible disc 402, thereby protecting the absorbent disc 112 and keeping the absorbent disc 112 at least partially non-saturated. This may prevent over saturation of the absorbent disc 112 adjacent the flexible disc 402 as the fluid absorbent surgical device 400 is inserted into the cannula.

Referring to FIG. 5B, as the fluid absorbent device 400 is pulled out of the cannula, the flexible disc 402 may flex in the opposite direction around the end cap 103 thereby exposing the absorbent disc 112 adjacent the flexible disc 402. Since the absorbent disc 112 adjacent the flexible disc 402 is protected by the flexible disc 402 as the fluid absorbent surgical device 400 is inserted into the cannula, the absorbent disc 112 may be in a non-saturated state that enables it to collect or scavenge the remaining fluid as the fluid absorbent surgical device 400 is pulled out of the cannula. While only illustrated in FIGS. 4-5B as a single flexible disc 402, one of ordinary skill in the art will appreciate that the fluid absorbent surgical device may comprise a plurality of flexible discs without departing from the scope of the disclosure. For example, two or more flexible discs may be disposed adjacent to the two or more absorbent discs 112.

Figure 6A:
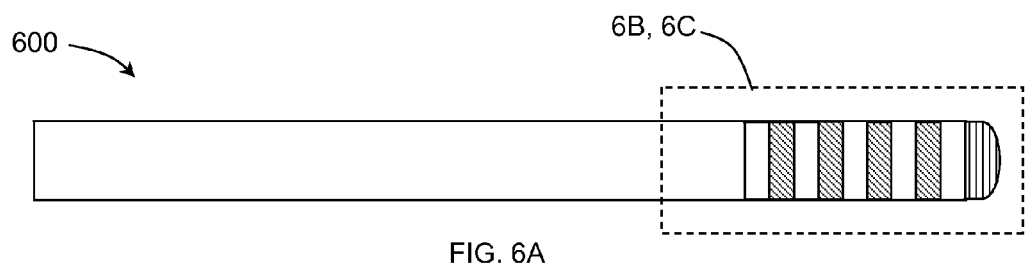
FIGS. 6A to 6C illustrate schematic views of embodiments of surgical devices.
Figure 6B:
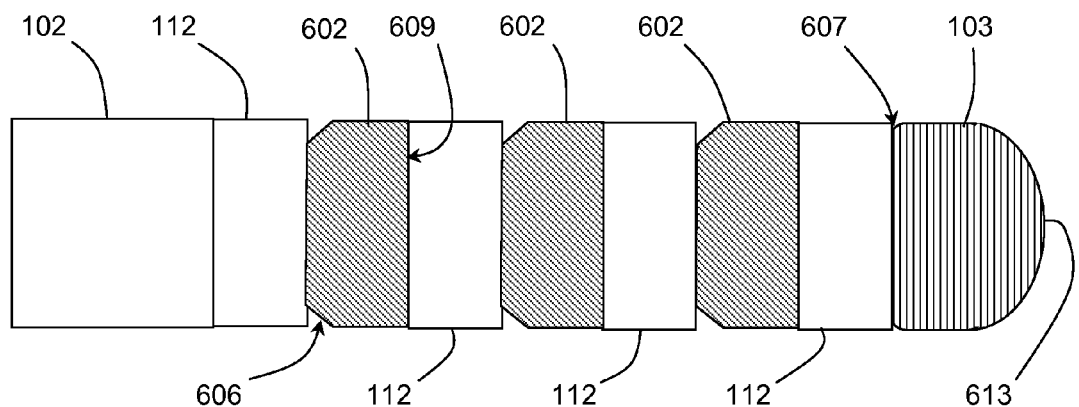
Figure 6C:
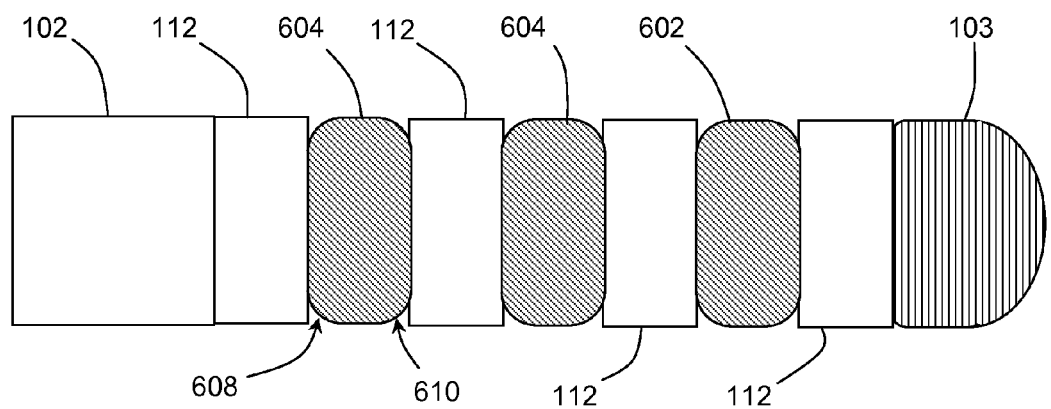

FIGS. 6A-6C illustrate another embodiment of a fluid absorbent surgical device 600. In an embodiment, the fluid absorbent surgical device 600 may be similar to the fluid absorbent surgical device 100 illustrated in FIG. 1, the surgical device 200 illustrated in FIGS. 2 and 3, and/or the surgical device 400 illustrated in FIGS. 4, 5A, and 5B, and similar components will not be described with respect to FIGS. 6A-6C in the interest of clarity. It should be understood that any of the embodiments and/or options described with respect to FIGS. 1-5B can also be used with the surgical device 600. In an embodiment, the fluid absorbent surgical device 600 is similar to the previously described fluid absorbent surgical devices except that the fluid absorbent surgical device 600 comprises spacers 602 having one or more edges that are tapered.

FIGS. 6B and 6C illustrate enlarged views of the fluid absorbent surgical device 600 of FIG. 6A. As shown in FIG. 6B, the spacers 602 may be shaped to allow the spacers 602 to pass through one or more restrictions (e.g., the valves, etc.) or openings (e.g., a distal tip, etc.) in the cannula without catching or hanging up on an edge of the opening or restriction. In an embodiment, at least one edge of at least one spacer 602 may have an outer diameter that is less than the maximum outer diameter of the spacer 602. In an embodiment, the edge 606 closest to the handle 102 may have a reduced outer diameter relative to the maximum outer diameter of the spacer 602. A variety of configurations may be used to provide the reduced diameter. In an embodiment, the edge 606 may be tapered, chamfered, beveled, arced, rounded, radiused, filleted, or the like to provide an edge 606 having a decreased diameter at the edge 606 nearest the handle 102. In some embodiments, the spacer 602 may be generally cylindrical in shape with only a portion at or near the edge 606 having a reduced diameter. In some embodiments, the entire spacer 602 may have a tapered, wedged, frusto-conical, trapezoidal, or similar shape to provide a reduced outer diameter at a first edge 606 relative to a second edge 609. In some embodiments, the edge 609 nearest the end cap 103 may have a reduced outer diameter relative to the maximum outer diameter of the spacer 602 in addition to or in place of the reduced diameter at the edge 606. The use of an edge having a reduced radius may allow the surgical device 600 to pass through one or more openings such as the valves, the end of the cannula, or the like without catching on an edge and moving or pulling the cannula out of the body. The decreased radius may also expose a portion of a side of the absorbent disc 112 to allow the fluid to be absorbed over a greater surface area of the absorbent disc 112.

As further illustrated in FIG. 6B, the proximal end 607 of the end cap 103 may also have a reduced diameter relative to the maximum outer diameter of the end cap 103. Any of the shapes or forms described above may be used with the end cap 103 to allow the end cap 103 to pass through a restriction or opening when being retracted from the cannula. In an embodiment, the distal end 613 of the end cap 103 may have a generally rounded or tapered shape. This shape may aid in guiding the surgical device 600 through the cannula as it is inserted into the cannula.

FIG. 6C illustrates a plurality of spacers 604 having both edges 608, 610 with reduced diameters relative to the maximum outer diameter of the spacers 604. This may allow the spacers to pass through one or more restrictions or opening without catching as the surgical instrument is both inserted into the cannula and retracted from the cannula. Any of the shapes of the edges described above can be used for the edge of the spacer 604.

Any suitable portion of the thickness (e.g., the axial length) of the spacer can have a reduced diameter to allow the surgical instrument to pass through the cannula. In an embodiment, the portion of the thickness of the spacer having a reduced outer diameter can comprise between about 1% to about 50%, about 5% to about 40%, or about 10% to about 20% of the thickness of the spacer. The amount of the outer diameter reduction may be selected to prevent the spacers from catching on a restriction or opening, and may depend on the maximum outer diameter of the surgical device 600, the inner diameter of any restrictions or openings, the materials used to form the spacers, and the like. In an embodiment, the radius at the edge of the spacer may be reduced between about 2% and 40%, between about 5% and about 30%, or between about 10% and about 20% relative to the maximum outer diameter of spacer.

Figure 7A:
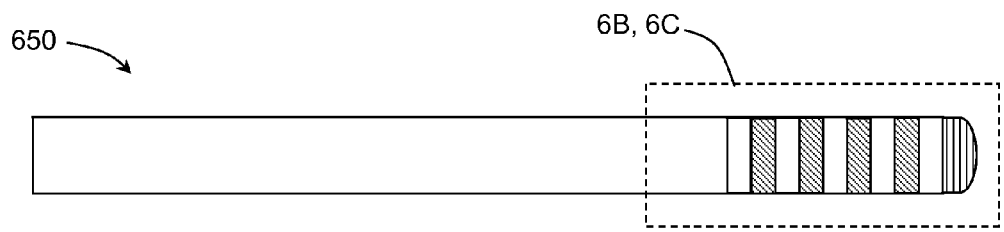
FIGS. 7A to 7C illustrate schematic views of another embodiment of a surgical device.
Figure 7B:
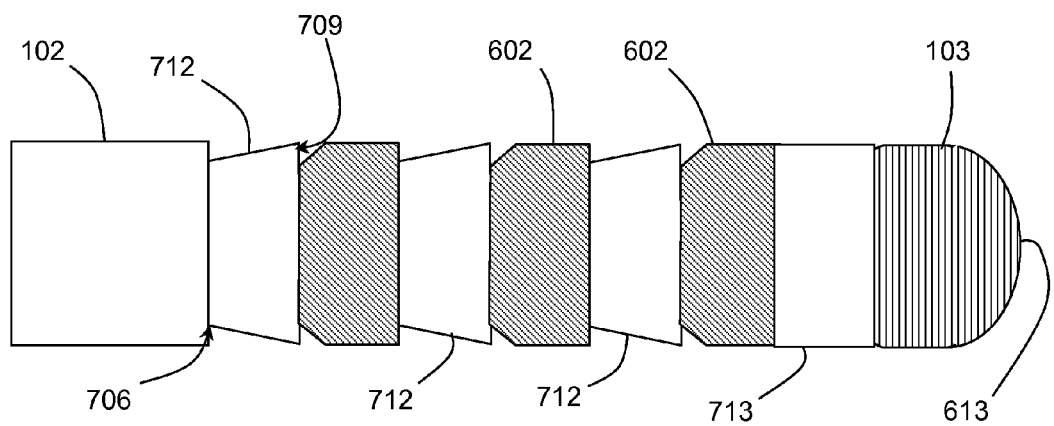

FIGS. 7A-7B illustrate another embodiment of a fluid absorbent surgical device 650. In an embodiment, the fluid absorbent surgical device 650 may be similar to the fluid absorbent surgical devices described with respect to FIG. 1-6C, and similar components will not be described with respect to FIGS. 7A-7C in the interest of clarity. It should be understood that any of the embodiments and/or options described with respect to FIGS. 1-6C can also be used with the surgical device 650. In an embodiment, the fluid absorbent surgical device 650 is similar to the previously described fluid absorbent surgical devices except that the fluid absorbent surgical device 650 comprises absorbent discs 712 that may not be cylindrical in shape.

Figure 7C:
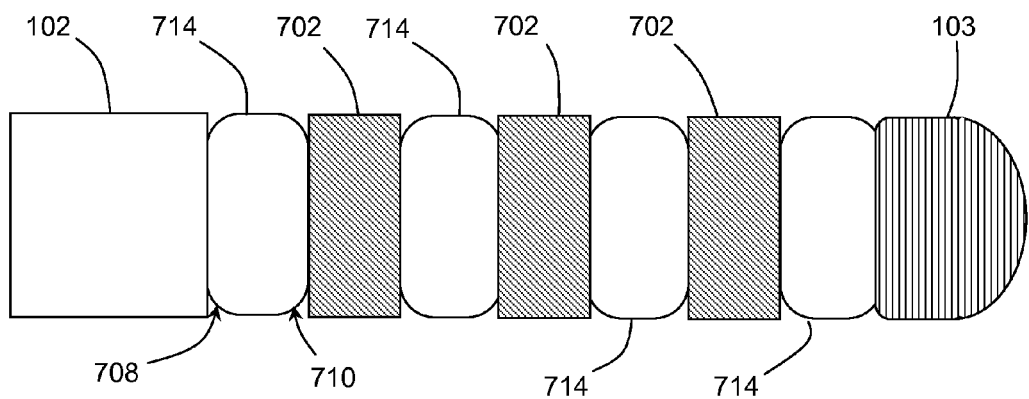

FIGS. 7B and 7C illustrate enlarged views of the fluid absorbent surgical device 650 of FIG. 7A. As shown in FIG. 7B, the absorbent discs 712 may be shaped as frusto-conical rings disposed about the post. The variation in shape may allow for a greater exposed surface area of the absorbent disc 712 to contact and absorb a fluid as well as guiding the surgical device 650 through the cannula. For example, the shape of the absorbent discs 712 may allow the absorbent discs 712 to pass through one or more restrictions (e.g., the valves, etc.) or openings (e.g., a distal tip, etc.) in the cannula without catching or hanging up on an edge of the opening or restriction. In an embodiment, at least one edge of at least one absorbent discs 712 may have an outer diameter that is less than the maximum outer diameter of the absorbent discs 712. In an embodiment, the edge 706 closest to the handle 102 may have a reduced outer diameter relative to the maximum outer diameter of the absorbent discs 712 (e.g., at a second edge 709). A variety of configurations may be used to provide the reduced diameter. As described with respect to the spacers, the edge 706 may be tapered, chamfered, beveled, arced, rounded, radiused, filleted, or the like to provide an edge 706 having a decreased diameter at the edge 706 nearest the handle 102. In some embodiments, the absorbent discs 712 may be generally cylindrical in shape with only a portion at or near the edge 706 having a reduced diameter. As shown in the embodiment of FIG. 7B, the entire absorbent discs 712 may have a tapered, wedged, frusto-conical, trapezoidal, or similar shape to provide a reduced outer diameter at a first edge 706 relative to a second edge 709. In some embodiment, the edge 709 nearest the end cap 103 may have a reduced outer diameter relative to the maximum outer diameter of the absorbent discs 712 in addition to or in place of the reduced diameter at the edge 706. The use of an edge having a reduced radius may allow the surgical device 650 to pass through one or more openings such as the valves, the end of the cannula, or the like without catching on an edge and moving or pulling the cannula out of the body.

As further illustrated in FIG. 7B, each of the absorbent discs 712 may have the same or different shapes. For example, one or more of the absorbent discs 713 may have a cylindrical shape while the remaining absorbent discs 712 may have a non-cylindrical shape. In an embodiment, one or more of the absorbent discs may have a first shape, and each of the remaining absorbent discs may have the same shape, a different shape, or any combination of shapes. Further, any of the options for the spacers 602 described above with respect to FIG. 6B may be used in combination with the shaped absorbent discs 712. For example, one or more of the spacers 602 may have a tapered edge in addition to the shaped absorbent discs 712.

FIG. 7C illustrates a plurality of absorbent discs 714 having both edges 708, 710 with reduced diameters relative to the maximum outer diameter of the absorbent discs 714. Any of the shapes of the edges described above can be used for the edge of the absorbent discs 714. When one or more of the edges 708, 710 are tapered, the outer diameter of the absorbent discs 714 may be slightly larger than the outer diameter of the spacers 702 and/or the inner diameter of the cannula. This may allow the absorbent discs 714 to contact the inner wall of the cannula while still being guided through the cannula by the reduced diameter portions.

In an embodiment, any suitable portion of the thickness (e.g., the axial length) of the absorbent disc 714 can have a reduced diameter to allow the surgical instrument to pass through the cannula. In an embodiment, the portion of the thickness of the absorbent disc having a reduced outer diameter can comprise between about 1% to about 50%, about 5% to about 40%, or about 10% to about 20% of the thickness of the absorbent disc 714. The amount of the outer diameter reduction may be selected to prevent the absorbent disc 714 from catching on a restriction or opening, and may depend on the maximum outer diameter of the surgical device 650, the inner diameter of any restrictions or openings, the materials used to form the absorbent disc, and the like. In an embodiment, the radius at the edge of the absorbent disc may be reduced between about 2% and 40%, between about 5% and about 30%, or between about 10% and about 20% relative to the maximum outer diameter of absorbent disc 714.

Figure 8:
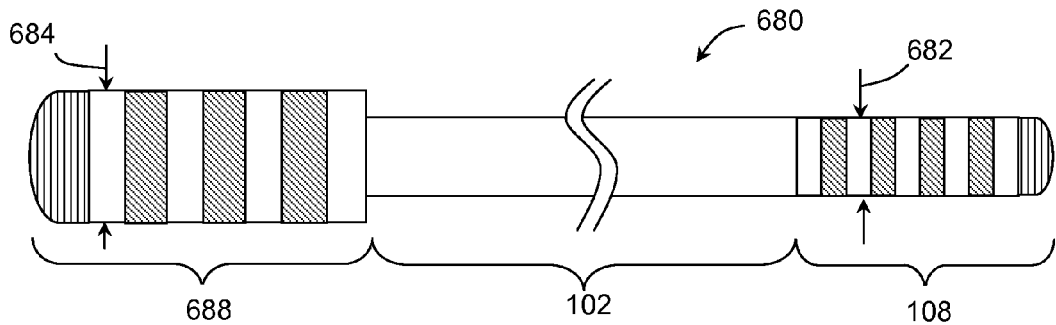
FIG. 8 illustrates still another embodiment of a surgical device.

FIG. 8 illustrate another embodiment of a fluid absorbent surgical device 680. In an embodiment, the fluid absorbent surgical device 680 may be similar to the fluid absorbent surgical devices described with respect to FIG. 1-7C, and similar components will not be described with respect to FIG. 8 in the interest of clarity. It should be understood that any of the embodiments and/or options described with respect to FIGS. 1-7C can also be used with the surgical device 680. In an embodiment, the fluid absorbent surgical device 680 is similar to the previously described fluid absorbent surgical devices except that the fluid absorbent surgical device 680 comprises two absorbent portions 108, 688, which may comprise the same or different diameters. For example, the first absorbent portion 108 may be used to clean a cannula with about a 5 millimeter diameter while the second absorbent portion 688 may be used to clean a cannula with about a 10 millimeter diameter.

As shown in FIG. 8, the first absorbent portion 108 may be disposed on a first end of the handle 102 and may be the same or substantially similar to any of the absorbent portions described herein, including any of the options described with respect to the absorbent discs, spacers, and/or the end cap. Similarly, a second absorbent portion 688 may be disposed on a second end of the handle 102 and may be the same or substantially similar to any of the absorbent portions described herein, including any of the options described with respect to the absorbent discs, spacers, and/or the end cap. In an embodiment, the first and second absorbent portions 108, 688 may be substantially similar in design and outer diameter, thereby allowing either end to be used with a given cannula. For example, when a first absorbent portion becomes saturated with fluid, the second absorbent portion may be used to provide additional absorption capacity and thereby absorb additional fluid. In some embodiments, the first and second absorbent portions 108, 688 may have different outer diameters. For example, the first absorbent portion 108 may have a smaller outer diameter 682 than the outer diameter 684 of the second absorbent portion 688. The diameters 682, 684 may comprise any of the outer diameters described with respect to the absorbent portions described herein. This may allow a single surgical device 680 to be used to clean cannulas having different inner diameters. Further, the designs of the spacers and/or absorbent discs may be the same or different along each absorbent portion 688, 108, which may allow for different cleaning abilities on each end. The use of a double-ended surgical device 680 may provide additional absorbent capacity, the ability to absorb fluid in different sized cannulas, and/or different cleaning abilities based on different designs of the spacers, absorbent discs, and/or end caps.

Figure 9:
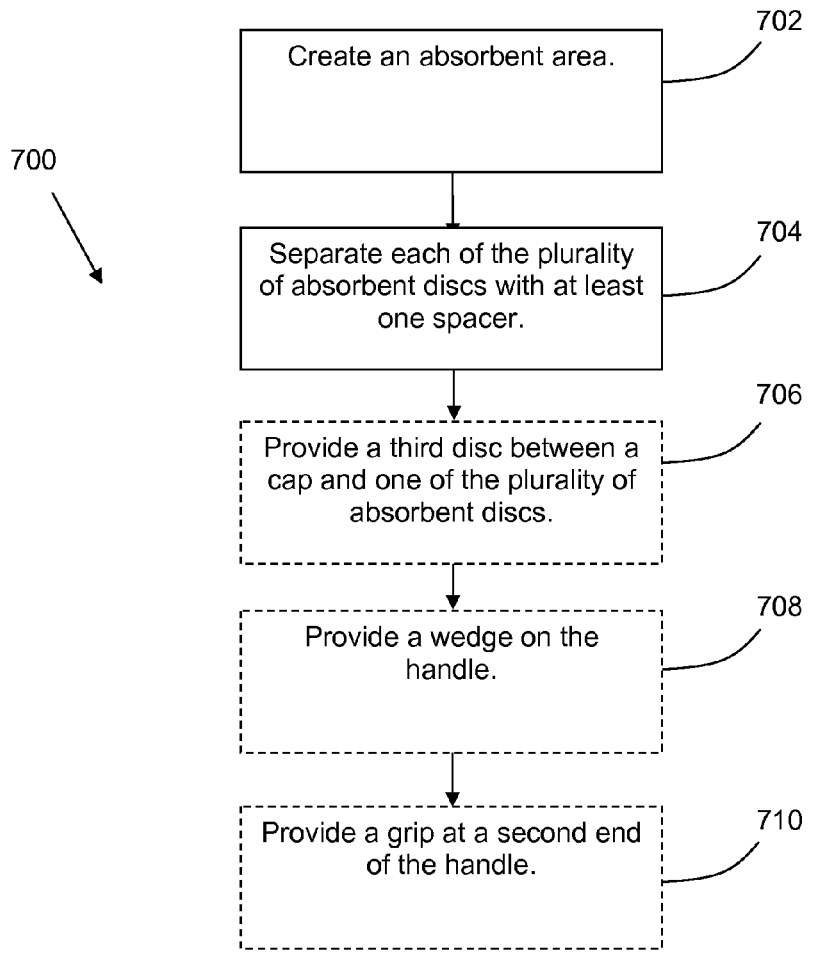
FIG. 9 illustrates a method of making a fluid absorbent surgical device according to an embodiment of the disclosure.

FIG. 9 illustrates a method 700 of making a fluid absorbent surgical device according to an embodiment of the disclosure. In this embodiment, an absorbent portion is created by placing a plurality of absorbent discs on at least one end of a handle (block 702). Each of the plurality of absorbent discs may be separated by at least one spacer of a plurality of spacers (block 704). In an embodiment, the plurality of absorbent discs and the plurality of spacers are approximately equivalent in size (e.g., diameter, thickness, etc.). A flexible disc may be provided between an end cap and one of the plurality of absorbent discs to shield the one of the plurality of absorbent discs as the fluid absorbent surgical device is inserted into the cannula (block 706). In an embodiment, the flexible disc is made a flexible non-absorbent material and is larger in diameter than the plurality of absorbent discs and the plurality of spacers, but smaller in thickness than the plurality of absorbent discs and the plurality of spacers. A wedge may be provided on the handle to indicate an optimal distance for inserting the absorbent portion into the cannula (block 708). A grip may be provided at a second end of the handle (block 710). Blocks 706, 708, and 710 may be optional as indicated by the hashed boxes.

In some embodiments, the absorbent portion may be formed by starting with an end cap coupled to a post. The absorbent discs and spacers can be placed onto the post in an alternating pattern. As the spacers are placed on the posts, they may be optionally coupled to the post to restrain the spacers from axial movement relative to the post. For example, an adhesive may be placed between the spacer and the post to adhere the spacers to the posts. When the desired number of absorbent discs and interposed spacers having been placed on the post, an exposed portion of the post may be disposed within an opening in an end of the handle. An adhesive may be disposed on the post and/or within the opening prior to disposing the post within the opening. Once the post is disposed within the opening, the end of the handle may retain the absorbent discs and spacers on the post. Any of the absorbent discs and/or spacers may comprise any of the configurations described herein. For example, the spacers may comprise a reduced outer radius at one or both edges.

In some embodiments, the absorbent portion may be formed by starting with a rod having spacers and gaps in between the spacers. The spacers can be integrally formed with the rod and/or coupled to the rod as described herein. An absorbent disc can then be formed within the gaps. For example, an absorbent material such as a foam can be injected into the gaps and allowed to cure. The resulting foam may be trimmed or otherwise processed to form the absorbent discs between the spacers. The trimming or processing may result in any of the configurations described herein. For example, the spacers may comprise a reduced outer radius at one or both edges and/or the absorbent discs may be cast or processed into a shape having a non-uniform outer radius.

Figure 10:
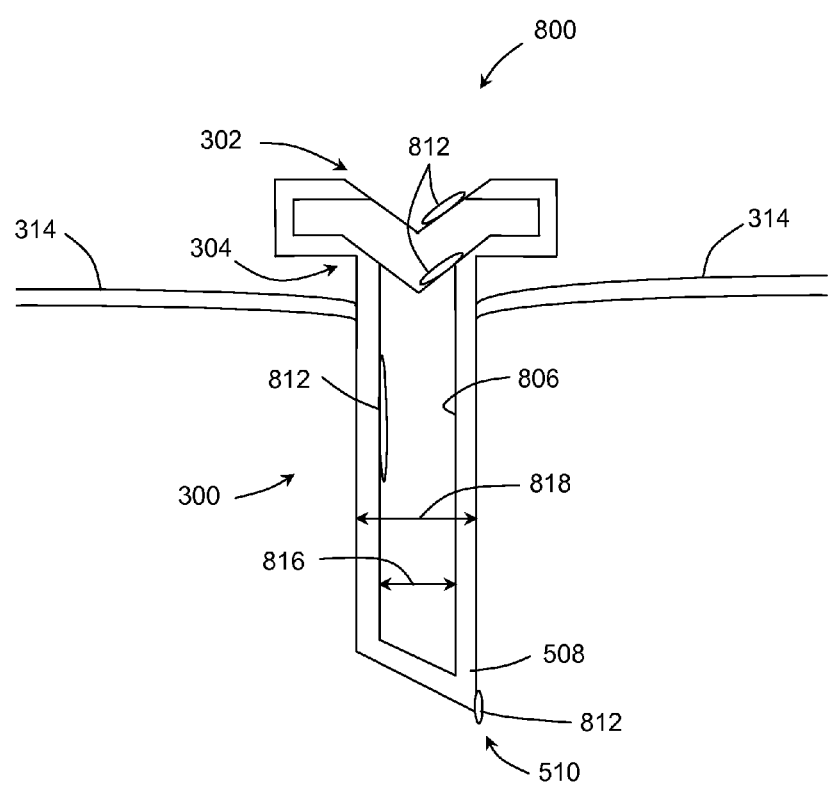
FIG. 10 illustrates a schematic view of a trocar/cannula according to an embodiment of the disclosure.

Once constructed, any of the surgical devices described herein may be used to remove at least a portion of a fluid on a surface of a cannula. As stated earlier, fluid materials become deposited on the surfaces of a cannula once it is inserted across an abdominal wall. As shown in FIG. 10, fluid materials 812 may become deposited along an outer valve 302, an inner valve 304, an inner wall 806, and an outer wall 508 of the distal tip 510 of a cannula 300 after it has been inserted across an abdominal wall 314. The distal end or tip for the purposes of this disclosure refers to the end of the cannula that is inserted into the body cavity. In this embodiment, the cannula has an inner diameter 816 and an outer diameter 818.

In an embodiment, a fluid absorbent surgical device can be inserted into the cannula 300. The surgical device can comprise any of the surgical devices described herein. The surgical device may be inserted beyond the outer valve 302 and the inner valve 304 of the cannula 300 and absorb the fluid materials 812 along the two valves. The surgical device may also be inserted along the inner wall 806 of the cannula 300 and absorb the fluid materials 812 along the inner wall 806. The absorbent discs may have an outer diameter that is approximately the same as or slightly smaller than the inner diameter 816 of the cannula 300. This allows the edges of the plurality of absorbent discs to sweep the inner wall 806 and absorb any fluid materials 812 along the inner wall 806. An optional marker, wedge, and/or other structure may be used to indicate an optimal distance for inserting the surgical device inside the cannula 300. As stated earlier, the optimal distance may be far enough to allow any fluid along the outer wall of the tip 510 to be absorbed without being inserted so far that the absorbent discs of the surgical device become saturated by coming into significant contact with fluid material that is not gathered on the cannula surfaces. Again, significant contact may be taken as having more than fifty percent of the absorbed fluid materials come from contact with bodily fluids that are not gathered on the surfaces of the cannula.

Figure 11:
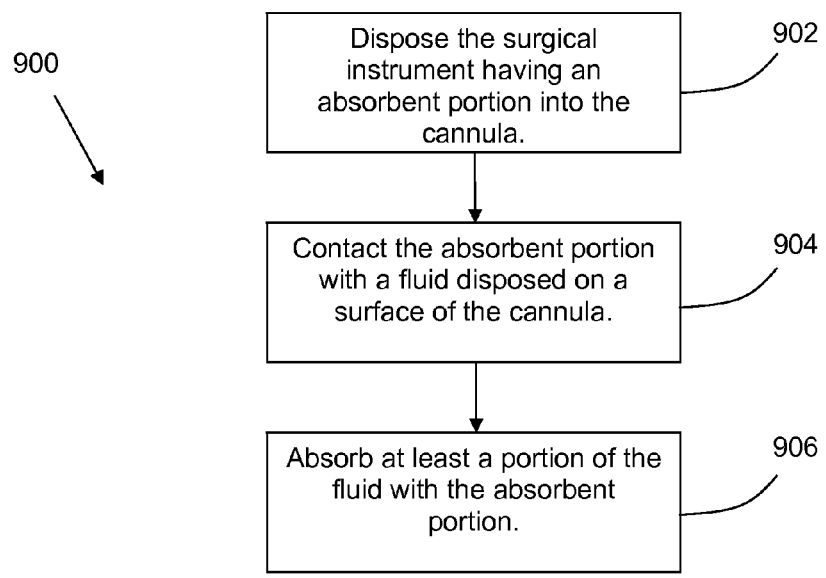
FIG. 11 illustrates a method of absorbing a fluid using an absorbent surgical device according to an embodiment of the disclosure.

In an embodiment, any of the surgical devices described herein may be used to sweep the cannula and absorb a fluid using a method 900 as illustrated in FIG. 11. The cannula can be swept by inserting the surgical device comprising the absorbent portion through the outer and inner valves of the cannula in step 902. The absorbent portion can be contacted with a fluid 812 disposed on a surface of the cannula 300 in step 904 and absorb at least a portion of the fluid with the absorbent portion in step 906. Because the absorbent portion may have an outer diameter that is approximately the same as or smaller than the inner diameter 816 of the cannula, the edges of the absorbent portion may pass along the inner walls of the cannula and absorb any fluid materials along the inner walls. The outer wall along a distal tip of the cannula is also swept by inserting at least a portion of the absorbent portion past the tip of the cannula. Because at least part of the absorbent portion is inserted beyond the tip of the cannula, the edges of the absorbent portion may extend beyond the tip of the cannula and absorb a fluid material adjacent or near the tip of the cannula.

In an embodiment, the absorbent portion comprises a plurality of absorbent discs and at least one spacer. The spacer can be restrained from axial movement relative to the plurality of absorbent discs. For example, the spacer can be adhered to the post to thereby prevent any axial movement along the post. This may prevent the spacer from moving axially and compressing an absorbent disc, which may cause any absorbed fluid to be emitted from the absorbent disc.

In an embodiment, a size of one or more of the absorbent discs may be selected to prevent the absorbent disc from deforming and potentially releasing absorbed fluid. As the surgical instrument is translated within the cannula, a force can be created on an outer surface of the plurality of absorbent discs. For example, the absorbent discs may contact the inner wall 806 of the cannula 300 and create a drag on the outer surface of the absorbent discs. The force may cause the absorbent disc to compress (e.g., resulting in the material bunching up), which can lead to a reduction in the absorbent capacity of the absorbent disc. The selection of the size of the absorbent discs may allow the absorbent discs to retain any of the absorbed fluid even when subject to the drag force. In an embodiment, each of the plurality of absorbent discs may have a ratio of a length of each absorbent disc to an outer diameter of each of the absorbent disc in a ratio of between about 1:2 and about 3:1. This may provide structural stability to allow the absorbent disc to be subject to drag without substantially deforming and releasing an absorbed fluid.

In an embodiment, an edge or side of one or more spacers may be tapered or beveled to aid in guiding the surgical instrument through the cannula. For example, at least a first edge of one of the spacers may have an outer diameter that is reduced relative to a maximum outer diameter of the spacer. In some embodiments, both edges of the spacer may have reduced outer diameters relative to the maximum outer diameter of the spacer. As the surgical instrument passes through the cannula 300, it may pass through one or more restrictions such as the valves 302, 304 and/or opening such as the distal tip 510. The edges of the spacers may be guided into the restrictions or openings based on the reduced diameter edges. For example, a beveled or chamfered edge may center and guide the surgical instrument through an opening rather than catch on the opening. This may help prevent the surgical instrument from becoming jammed or damaged during use.

While a number of the embodiments described above disclose the fluid absorbent surgical device comprising a plurality of absorbent discs, in alternate embodiments, the fluid absorbent surgical device may comprise a plurality of linear strips of absorbent material secured to the handle in addition to or in lieu of the plurality of absorbent discs. The plurality of linear strips of absorbent material may be secured to the handle using an adhesive. In another alternative embodiment, in addition to or in lieu of the plurality of absorbent discs, the second part of the handle may be fenestrated and absorbent material may be placed inside the second part of the handle. For example, the second part of the handle may comprise a plurality of holes. In such an alternative embodiment, as the fluid absorbent surgical device is inserted through a cannula, the fluid material may be pulled into the plurality of holes of the second part of the handle by capillary action and the absorbent material inside the second part of the handle may hold or absorb the fluid material.

Additional alternatives may also be used. For example, the absorbent portion could be formed with a continuous absorbent surface along its exterior. Furthermore, one of ordinary skill in the art would also recognize that any method or system for removing fluid materials from the surfaces of the cannula could be used. For instance, inserting a surface that pushes or squeezes, rather than actually absorbing, the fluid materials from the surfaces could also be used. As one example, a water-repellant area may be formed by a plurality of rubber, or other water-resistant, discs. These water-resistant discs would have flexibility along their edges that would allow them to bend and flex along the surfaces of the cannula with a proximity that was close enough to push or squeeze any fluid materials from a surface or multiple surfaces of the cannula. Also, while the above embodiments describe spacers as one way of separating the absorbent discs, one of ordinary skill in the art would recognize that alternate systems and methods of providing separation between the absorbent discs may be used. For example, one could separate the second absorbent discs simply by placing one or more of the absorbent discs between each of the spacers. Furthermore, while the above embodiments disclose specific orientations of the absorbent discs and the spacers, one of ordinary skill in the art would recognize that any number and/or combination of the absorbent discs and the spacers may be used.

Although the use of the surgical device of the disclosure is described in the context of laparoscopic surgery, one of ordinary skill in the art would recognize that it could also be used in other endoscopic or minimally invasive procedures, such as thoracoscopic surgery.

Various systems, devices, and methods for surgical instruments and uses thereof have been described. The following are some of the non-limiting, specific embodiments in accordance with the present disclosure:

In a first embodiment, a surgical device that absorbs fluid material on a surface of a cannula comprises a handle, and an absorbent portion coupled to a first end of the handle. The absorbent portion comprises a plurality of absorbent discs separated by at least one spacer. The plurality of absorbent discs and the at least one spacer are disposed about a post, and the at least one spacer is adhered to the post. In a second embodiment, the at least one spacer and the plurality of absorbent discs of the first embodiment may comprise approximately the same outer diameter. In a third embodiment, the handle of the first or second embodiment may comprise an opening configured to receive the post, the post may be engaged with the opening, and the absorbent portion may be coupled to the first end of the handle based on the engagement between the post and the opening. In a fourth embodiment, the absorbent portion of any of the first to the third embodiments may also include an end cap, and the plurality of absorbent discs and the at least one spacer may be retained between the end cap and the first end of the handle. In a fifth embodiment, at least one edge of the at least one spacer of any of the first to fourth embodiments may comprise a reduced outer diameter relative to a maximum outer diameter of the at least one spacer. In a sixth embodiment, at least one edge of the at least one spacer of any of the first to fifth embodiments may be tapered. In a seventh embodiment, the absorbent portion of any of the first to sixth embodiments may be formed from a foam, cotton, a cellulosic material, or any combination thereof. In an eighth embodiment, the surgical device of any of the first to seventh embodiments may also include a second absorbent portion coupled to a second end of the handle, and the absorbent portion may comprise a plurality of absorbent discs separated by at least one spacer. In a ninth embodiment, an outer diameter of the absorbent portion of the eighth embodiment may be different than an outer diameter of the second absorbent portion.

In a tenth embodiment, a surgical device that absorbs fluid material on a surface of a cannula comprises a handle, and an absorbent portion coupled to a first end of the handle. The absorbent portion comprises a plurality of absorbent discs separated by at least one spacer, and a ratio of a length of a first absorbent disc of the plurality of absorbent disc to an outer diameter of the first absorbent disc is in a ratio of between about 1:2 and about 3:1. In an eleventh embodiment, the plurality of absorbent discs and the at least one spacer of the tenth embodiment may have a substantially similar outer diameter. In a twelfth embodiment, the outer diameter of the first absorbent disc of the tenth or eleventh embodiment may be between about 3 mm and about 15 mm. In a thirteenth embodiment, the length of the first absorbent disc of any of the tenth to twelfth embodiments may be between about 1 mm and about 20 mm. In a fourteenth embodiment, the plurality of absorbent discs of any of the tenth to thirteenth embodiments may approximate the inner diameter of the cannula. In a fifteenth embodiment, the plurality of absorbent discs and the at least one spacer of any of the tenth to fourteenth embodiments may be disposed about a post, and the at least one spacer may be adhered to the post. In a sixteenth embodiment, the first absorbent disc of the fifteenth embodiment may not be adhered to the post. In a seventeenth embodiment, the absorbent of any of the tenth to sixteenth embodiments may be formed from a foam, cotton, a cellulosic material, or any combination thereof. In an eighteenth embodiment, the at least one spacer of any of the tenth to seventeenth embodiments may comprise a non-absorbent material.

In a nineteenth embodiment, a surgical device that absorbs fluid material on a surface of a cannula comprises a handle, and an absorbent portion coupled to a first end of the handle. The absorbent portion comprises a plurality of absorbent discs separated by at least one spacer. The at least one spacer has a first edge, and the first edge has an outer diameter that is reduced relative to a maximum outer diameter of the at least one spacer. In a twentieth embodiment, each of the plurality of absorbent discs of the nineteenth embodiment may be separated by at least one spacer. In a twenty first embodiment, the first edge of the nineteenth or twentieth embodiment may be tapered, chamfered, beveled, arced, rounded, radiused, filleted, or any combination thereof. In a twenty second embodiment, the at least one spacer of any of the nineteenth to twenty first embodiments may have a second edge opposite the first edge, and the second edge has an outer diameter that is reduced relative to the maximum outer diameter of the at least one spacer. In a twenty third embodiment, the at least one spacer of any of the nineteenth to twenty second embodiments may be restrained from axial movement relative to the plurality of absorbent discs. In a twenty fourth embodiment, the at least one spacer of any of the nineteenth to twenty third embodiments may comprise a non-absorbent material. In a twenty fifth embodiment, a ratio of a length of a first absorbent disc of the plurality of absorbent disc to an outer diameter of the first absorbent disc of any of the nineteenth to twenty fourth embodiments may be in a ratio of between about 1:2 and about 3:1. In a twenty sixth embodiment, at least one absorbent disc of the plurality of absorbent discs of any of the nineteenth to twenty fifth embodiments may have a first absorbent disc edge, and the first absorbent disc edge may have an outer diameter that is reduced relative to a maximum outer diameter of the at least one absorbent disc.

In a twenty seventh embodiment, a method of absorbing fluid in a cannula comprises disposing a surgical device into a cannula, contacting the absorbent portion with a fluid disposed on a surface of the cannula, and absorbing at least a portion of the fluid with the absorbent portion. The surgical device comprises an absorbent portion comprising a plurality of absorbent discs separated by at least one spacer, and the at least one spacer is restrained from axial movement relative to the plurality of absorbent discs. In a twenty eighth embodiment, the method of the twenty seventh embodiment may also include translating the surgical device within the cannula, creating a force on an outer surface of the plurality of absorbent discs in response to the translating, and retaining the absorbed portion of the fluid within the plurality of absorbent discs subject to the force. In a twenty ninth embodiment, each of the plurality of absorbent discs of the twenty eighth embodiment may have a ratio of a length of each absorbent disc to an outer diameter of each of the absorbent disc in a ratio of between about 1:2 and about 3:1, and the absorbed portion of the fluid is retained within the plurality of absorbent discs under the force based on the ratio of the length of each absorbent disc to the outer diameter of each of the absorbent disc. In a thirtieth embodiment, the at least one spacer of any of the twenty seventh to twenty ninth embodiments may have a first edge, and the first edge may have an outer diameter that is reduced relative to a maximum outer diameter of the at least one spacer. In a thirty first embodiment, the method of the thirtieth embodiment may also include passing the surgical device through a restriction or opening, and guiding the absorbent portion through the restriction or opening based on the reduced outer diameter of the first edge of the at least one spacer.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A surgical device that absorbs fluid material on a surface of a cannula, the surgical device comprising:
    a handle; and
    an absorbent portion coupled to a first end of the handle, wherein the absorbent portion comprises a plurality of absorbent discs separated by at least one spacer, wherein the plurality of absorbent discs and the at least one spacer are disposed about a post, and the at least one spacer is restrained from axial movement relative to the post, and wherein at least an edge of the at least one spacer closest to the handle comprises a reduced outer diameter relative to a maximum outer diameter of the at least one spacer.

2. The surgical device of claim 1, wherein the at least one spacer and the plurality of absorbent discs comprise approximately the same outer diameter.

3. The surgical device of claim 1, wherein the handle comprises an opening configured to receive the post, wherein the post is engaged with the opening, and wherein the absorbent portion is coupled to the first end of the handle based on the engagement between the post and the opening.

4. The surgical device of claim 1, wherein the at least one edge of the at least one spacer is tapered.

5. The surgical device of claim 1, wherein the absorbent portion is formed from a foam, cotton, a cellulosic material, or any combination thereof.

6. A surgical device that absorbs fluid material on a surface of a cannula, the surgical device comprising:
    a handle; and
    an absorbent portion coupled to a first end of the handle, wherein the absorbent portion comprises a plurality of absorbent discs separated by at least one spacer, wherein a ratio of a length of a first absorbent disc of the plurality of absorbent disc to an outer diameter of the first absorbent disc is in a ratio of between about 1:2 and about 3:1, and wherein at least an edge of the at least one spacer closest to the handle comprises a reduced outer diameter relative to a maximum outer diameter of the at least one spacer.

7. The surgical device of claim 6, wherein the plurality of absorbent discs and the at least one spacer have a substantially similar outer diameter.

8. The surgical device of claim 6, wherein the plurality of absorbent discs approximate the inner diameter of the cannula.

9. The surgical device of claim 6, wherein the plurality of absorbent discs and the at least one spacer are disposed about a post, and wherein the at least one spacer is adhered to the post.

10. The surgical device of claim 9, wherein the first absorbent disc is not adhered to the post.

11. The surgical device of claim 6, wherein the absorbent portion is formed from a foam, cotton, a cellulosic material, or any combination thereof.

12. The surgical device of claim 6, wherein the at least one spacer comprises a non-absorbent material.

13. A surgical device that absorbs fluid material on a surface of a cannula, the surgical device comprising:
    a handle; and
    an absorbent portion coupled to a first end of the handle, wherein the absorbent portion comprises a plurality of absorbent discs separated by at least one spacer, wherein the at least one spacer has a first edge closest to the handle, and wherein the first edge has an outer diameter that is reduced relative to a maximum outer diameter of the at least one spacer.

14. The surgical device of claim 13, wherein each of the plurality of absorbent discs is separated by one or more spacers.

15. The surgical device of claim 13, wherein the first edge is tapered, chamfered, beveled, arced, rounded, radiused, filleted, or any combination thereof.

16. The surgical device of claim 13, wherein the at least one spacer has a second edge opposite the first edge, and wherein the second edge has an outer diameter that is reduced relative to the maximum outer diameter of the at least one spacer.

17. The surgical device of claim 13, wherein the at least one spacer is restrained from axial movement relative to the plurality of absorbent discs.

18. The surgical device of claim 13, wherein the at least one spacer comprises a non-absorbent material.

19. The surgical device of claim 13, wherein a ratio of a length of a first absorbent disc of the plurality of absorbent disc to an outer diameter of the first absorbent disc is in a ratio of between about 1:2 and about 3:1.

* * * * *